United States Patent [19]

Cliffe et al.

[11] Patent Number: 5,169,845
[45] Date of Patent: Dec. 8, 1992

[54] PIPERAZINE DERIVATIVES

[75] Inventors: Ian A. Cliffe, Slough; Graham J. Warrellow, Stanmore, both of England

[73] Assignee: John Wyeth & Brother Limited, Maidenhead, England

[21] Appl. No.: 768,146

[22] Filed: Sep. 30, 1991

[30] Foreign Application Priority Data

Oct. 19, 1990 [GB] United Kingdom ............... 9022821

[51] Int. Cl.$^5$ ............... A61K 31/395; A61K 31/495; C07D 403/06; C07D 403/14
[52] U.S. Cl. ............... 514/212; 514/235.8; 514/236.2; 514/236.5; 514/252; 514/253; 540/598; 544/121; 544/238; 544/295; 544/360; 544/361; 544/364; 544/366; 544/370; 544/372; 544/379; 544/359
[58] Field of Search ............... 540/598; 544/360, 364, 544/361, 357, 359, 366, 372, 295, 238, 121, 379, 370; 514/252, 212, 253, 235.8, 236.2, 226.5

[56] References Cited

U.S. PATENT DOCUMENTS

| | | | |
|---|---|---|---|
| 4,882,432 | 11/1989 | Abou-Gharbia et al. | 544/360 |
| 4,921,958 | 5/1990 | Abou-Gharbia et al. | 544/295 |
| 4,968,684 | 11/1990 | Van Daele et al. | 544/360 |
| 4,988,814 | 1/1991 | Abou-Gharbia et al. | 544/360 |

OTHER PUBLICATIONS

Morren et al., Chem. Abst., 59:87326 (1963).

Primary Examiner—Cecilia Tsang
Attorney, Agent, or Firm—Arthur G. Seifert

[57] ABSTRACT

Piperazine derivative of formula

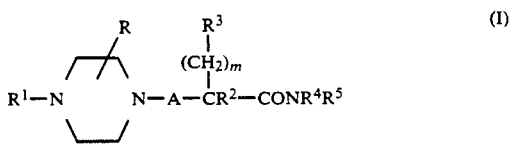

(I)

and the pharmaceutically acceptable acid addition salts, where A is an alkylene chain of 1 or 2 carbon atoms optionally substituted by one or more lower alkyl groups, m is 0, 1 or 2, R is hydrogen or lower alkyl, $R^1$ is aryl or a mono- or bicyclic heteroaryl radical, $R^2$ is hydrogen or lower alkyl, $R^3$ is a heteroaryl radical, $R^4$ is hydrogen, lower alkyl or aryl, and $R^5$ is hydrogen, lower alkyl, cycloalkyl, cycloalkyl(lower)alkyl, aryl, or aryl(lower)alkyl or $R^4$ and $R^5$ together with the nitrogen atom to which they are both attached represent a saturated heterocyclic ring which may contain a further hetero atom are 5—$HT_{1A}$-binding agents and may be used, for example, as anxiolytics.

9 Claims, No Drawings

PIPERAZINE DERIVATIVES

This invention relates to piperazine derivatives, to processes for their preparation, to their use and to pharmaceutical compositions containing them. The novel compounds act on the central nervous system by binding to 5-HT receptors (as more fully explained below) and hence can be used as medicaments for treating humans and other mammals.

The novel compounds of the invention are those of the general formula

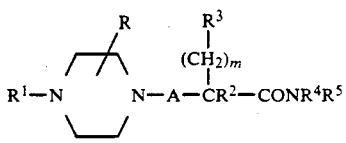

and the pharmaceutically acceptable acid addition salts thereof.

In formula (I)
m is 0, 1 or 2,
A is an alkylene chain of 1 or 2 carbon atoms optionally substituted by one or more lower alkyl groups,
R is hydrogen or lower alkyl,
$R^1$ is aryl or a mono- or bicyclic heteroaryl radical,
$R^2$ is hydrogen or lower alkyl,
$R^3$ is a heteroaryl radical,
$R^4$ is hydrogen, lower alkyl or aryl,
and $R^5$ is hydrogen, lower alkyl, cycloalkyl, cycloalkyl(lower)alkyl, aryl, or aryl(lower)alkyl or $R^4$ and $R^5$ together with the nitrogen atom to which they are both attached represent a saturated heterocyclic ring which may contain a further hetero atom.

The term lower as used herein means that the radical referred to contains 1 to 6 carbon atoms. Preferably such radicals contain 1 to 4 carbon atoms. Examples of "lower alkyl" are methyl, ethyl, propyl, isopropyl, butyl, isobutyl, tert.-butyl, pentyl and isopentyl.

When used herein aryl means an aromatic radical having 6 to 12 carbon atoms (e.g. phenyl or naphthyl) which optionally may be substituted by one or more substituents. For example, $R^1$ may be a phenyl or naphthyl radical optionally substituted by one or more lower alkyl, lower alkoxy (e.g. methoxy, ethoxy, propoxy, butoxy), halogen, halo(lower)alkyl (e.g. trifluoromethyl), nitro, amino, (lower)alkylamino or di(lower)alkylamino substituents. Preferably the aryl radical $R^1$ contains a substituent (e.g. lower alkoxy) in the ortho position. A particularly preferred example of $R^1$ is o-(lower)alkoxyphenyl (e.g. o-methoxyphenyl).

The term 'heteroaryl' refers to an aromatic radical containing one or more hetero ring atoms (e.g. oxygen, nitrogen, sulphur) and which may be optionally substituted by one or more substituents. Preferred examples of substituents are given above in connection with "aryl" radicals. Preferably the hetero ring contains a nitrogen hetero atom with or without further hetero atoms. The heteroaryl radical may be mono- or bicyclic and contain, for example, 5 to 11 ring atoms. A monocyclic radical may, for example, contain 5 to 7 ring atoms and a bicyclic radical may contain 9 to 11 ring atoms. When $R^1$ is heteroaryl it is preferably a monocyclic radical, such as optionally substituted pyridinyl, pyrimidinyl or pyrazinyl, or a bicyclic radical, such as quinolinyl or isoquinolinyl. Examples of the heteroaryl group $R^3$ are optionally substituted pyridinyl, pyrimidinyl, pyrazinyl, imidazolyl, pyrazolyl, quinolinyl, triazolyl, tetrazolyl, thienyl and furyl. These groups may be connected to the remainder of the molecule via a ring heteroatom or a ring C atom.

A cycloalkyl group can contain 3 to 12 carbon atoms.

When $R^3$ and $R^4$ together with the nitrogen atom to which they are attached form a heterocyclic ring this may be, for example, azetidino, pyrrolidino, piperidino, hexahydroazepino, morpholino or piperazino which may be optionally substituted by, for example, lower alkyl, aryl or aryl(lower)alkyl.

Examples of the radical —A— include —$CH_2$—, —$CH(CH_3)$—, —$C(CH_3)_2$—, —$CH_2CH_2$—, —$CH(CH_3)$—$CH_2$—, —$CH_2CH(CH_3)$—, —$C(CH_3)_2$—$CH_2$ and $CH_2C(CH_3)_2$—.

Preferred compounds are:
those in which $R^1$ is aryl particularly an optionally substituted phenyl such as o-methoxyphenyl;
those in which $R^2$ is hydrogen;
those in which $R^3$ is 2- or 4-pyridinyl or imidazolyl and
those in which —$NR^4R^5$ represents a cyclic grouping e.g. piperidino or hexahydroazepino.

The compounds of the invention may be prepared by a number of methods known in the art from known starting materials or starting materials that may be prepared by conventional methods. In one method for preparing an amide of formula (I), an amine of formula $$NHR^4R^5 \quad (II)$$

where $R^4$ and $R^5$ are as defined above is acylated with an acid of formula

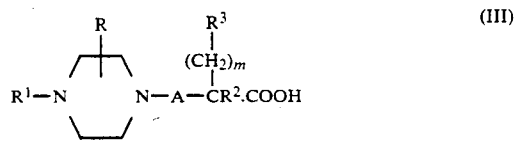

(where m, A, R, $R^1$, $R^2$ and $R^3$ are as defined above) or with an acylating derivative thereof. Examples of acylating derivatives include the acid halides (e.g. acid chlorides), azides, anhydrides, imidazolides (e.g. obtained from 1,1'-carbonyldiimidazole), esters (particularly activated esters) or O-acyl ureas obtained from a carbodiimide such as a dialkylcarbodiimide particularly dicyclohexylcarbodiimide. Preferably the amine is acylated with the acid in presence of a coupling agent such as 1,1'-carbonyldiimidazole, iso-butylchloroformate or diphenylphosphinyl chloride.

The acids of formula (III) or their acylating derivatives may be prepared by known methods. For example the acid may be prepared by hydrolysis of a corresponding ester.

Alternatively the acids may be prepared by reaction of carbon dioxide with the anion of a compound of formula

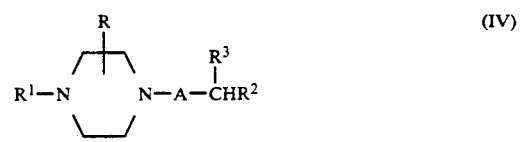

(where A, R, $R^1$, $R^2$ and $R^3$ are as defined above). The anion may be prepared by reaction of the compound of formula (IV) with a strong base, e.g. n-butyl lithium.

Compounds of the invention in which m is O, $R^3$ is an electron withdrawing group such as 2-quinolinyl, 2-pyridyl, 2-pyrimidinyl, 2-pyrazinyl and $R^4$ is hydrogen may be prepared by reacting the anion of the compound of formula (IV) with an isocyanate of formula $R^5NCO$.

An alternative method of preparing the compounds of the invention comprises alkylation of a piperazine of formula

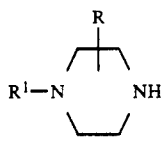     (VI)

(where R and $R^1$ are as defined above) with an alkylating agent providing the group

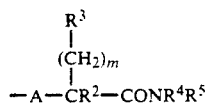     (VII)

(where m, A, $R^2$, $R^3$, $R^4$ and $R^5$ are as defined above).

The alkylating agent may be, for example, a compound of formula

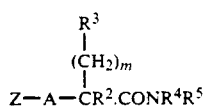     (VIII)

where A, $R^2$, $R^3$, $R^4$ and $R^5$ are as defined above and Z is a leaving group such as halogen or an alkyl- or arylsulphonyloxy group. Alternatively the alkylating agent may be an unsaturated compound of formula

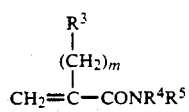     (IX)

where m, $R^3$, $R^4$ and $R^5$ are as defined above and the compound of formula (IX) is reacted with the piperazine of formula (VI) by means of a Michael reaction.

An alternative method of preparing the compounds of the invention (particularly the tertiary amides) comprises reaction of the anion of a compound of formula (X)

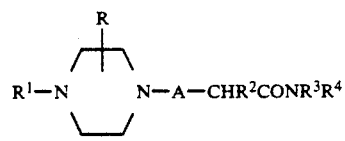     (X)

where A, R, $R^1$, $R^2$, $R^3$ and $R^4$ have the meanings given above, with a compound of formula

     (XI)

where $R^3$ and m have the meanings given above and Y is a leaving group, e.g. halogen. The anion of the compound of formula (X) may be obtained by reaction of the compound with a strong base e.g. lithium diisopropylamide or potassium bis(trimethylsilyl)amide.

A further method of preparing the compounds of the invention comprises reaction of the anion of a compound of formula (XII)

     (XII)

where m, $R^2$, $R^3$ and $R^4$ are as defined above with a compound of formula (XIII)

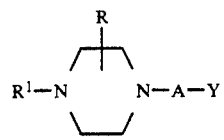     (XIII)

where A, R, $R^1$ and Y are as defined above. The anion of the compound of formula XII can be prepared by reaction of the compound with a strong base (e.g. an alkali metal hydride).

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of such as anxiety in mammals, particularly humans. They may also be useful as antidepressants, hypotensives and as agents for regulating the sleep/wake cycle, feeding behaviour and/or sexual function.

The compounds of the invention were tested for 5-$HT_{1A}$ receptor binding activity in rat hippocampal membrane homogenate by the method of B S Alexander and M D Wood, J Pharm Pharmacol, 1988, 40, 888-891. N-tert.-Butyl-3-[4-(2-methoxyphenyl)piperazin-1-yl]-2-(2pyridyl)propanamide and 2,3,4,5,6,7-hexahydro-1-[2-(2-thiophenyl)-4-(1-(4-(2-methoxyphenyl)-piperazinyl))]butyryl-1H-azepine, representative compounds of the invention, have $IC_{50}$ of 38 nM and 0.8 nM respectively in this test.

The affinity for the $\alpha_1$-ite (as measured by the procedure of A L Marrow et al, Mol. Pharmacol., 1986, 29, 321) for the above compounds are, respectively $IC_{50}$ 2897 nM and 147 nM.

The invention also provides a pharmaceutical composition comprising a compound of formula (I) or a pharmaceutically acceptable acid addition salt thereof in association with a pharmaceutically acceptable carrier. Any suitable carrier known in the art can be used to prepare the pharmaceutical composition. In such a composition, the carrier is generally a solid or liquid or a mixture of a solid or liquid.

Solid form compositions include powders, granules, tablets, capsules (e.g. hard and soft gelatine capsules), suppositories and pessaries. A solid carrier can be, for example, one or more substances which may also act the process is a free base an acid addition salt, particularly a pharmaceutically acceptable acid addition salt, may be obtained by dissolving the free base in a suitable organic solvent and treating the solution with an acid, in accordance with conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic, p-toluenesulphonic, oxalic and succinic acids.

The compounds of the invention contain one or more asymmetric carbon atoms, so that the compounds can exist in different steroisomeric forms. The compounds can be, for example, racemates or optically active forms. The optically active forms can be obtained by resolution of the racemates or by asymmetric synthesis.

The compounds of the present invention possess pharmacological activity. In particular, they act on the central nervous system by binding to 5-HT receptors. In pharmacological testing it has been shown that the compounds particularly bind to receptors of the 5-$HT_{1A}$ type. In general, the compounds selectively bind to receptors of the 5-$HT_{1A}$ type to a much greater extent than they bind to other receptors such as $\alpha_1$. Many exhibit activity as 5-HT1A antagonists in pharmacological testing. The pharmacological testing of the compounds indicates that they can be used for the treatment of CNS disorders, as flavouring agents, lubricants, solubilisers, suspending agents, fillers, glidants, compression aides, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term composition. is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols, e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged composition, for example packeted powders, vials, ampoules, prefilled syringes or sachets containing liquid. The unit dosage form can be, for example, a capsule or tablet itself, or it can be the appropriate number of any such compositions in package form. The quantity of the active ingredient in unit dose of composition may be varied or adjusted from 0.5 mg or less to 750 mg or more, according to the particular need and the activity of the active ingredient.

The following Examples illustrate the invention:

EXAMPLE 1

N-tert-Butyl-3-[4-(2-methoxyphenyl)piperazin-1-yl]-2-(2-pyridyl)propanamide 1-(2-Methoxyphenyl)-4-[1-(2-pyridyl)ethyl]piperazine (1.229 g, 4.13 mmol) was dissolved in anhydrous THF (10 ml) and the solution cooled to −70° C. n-Butyl-lithium (1.6M solution, 2.9 ml, 4.6 mmol, 1.1 equiv.) was added dropwise. After 0.25 h., tert-butylisocyanate (0.60 g, 6.0 mmol) in THF (2 ml) was added and the reaction mixture allowed to warm to room temperature over 1 h. The mixture was poured into water (10 ml), extracted with dichloromethane ( 2×50 ml), washed with brine (25 ml), dried ($Na_2SO_4$), and concentrated in vacuo to give a brown oil. This was dissolved in di-isopropylether and treated with charcoal. The mixture was filtered and allowed to crystallise to afford the title compound as the 1.5 hydrate (1.41 g 86%), m.p. 138°–139° C. with partial melt at 123° C. (Found: C,65.5;H,8.15;N,13.2. $C_{23}H_{32}N_4O_2.1.5H_2O$ requires C,65.2;H,8.3;N,13.2%).

EXAMPLE 2

2,3,4,5,6,7-Hexahydro-1-[2-(2-thiophenyl)-4-(1-(4-(2-methoxyphenyl)piperazinyl))]butyryl-1H-azepine A stirred suspension of potassium hydride, 35 wt % suspension in mineral oil (1.94 g, ca. 16.9 mmol) in DMF (10 ml) was treated dropwise under Ar with 2,3,4,5,6,7-hexahydro-1[2-(2-thiophenyl)acetyl]-1H-azepine (2.21 g, 9.9 mmol) in DMF (8 ml). Immediate occurred. After 10 min, a solution of 1-(2-chloroethyl)-4-(2-methoxyphenyl)piperazine (1.95 g, 7.7 mmol) in DMF (10 ml) was added. After 6 hr, the reaction was quenched with water (100 ml) and extracted with ethyl acetate (2×100 ml). The extracts were washed with water (2×100 ml), dried ($MgSO_4$), and evaporated in vacuo. The residue was chromatographed (silica; ethyl acetate), the yellow oil dissolved in methanol (5 ml), and the solution acidified with 1N-HCl in ether. Evaporation in vacuo followed by crystallisation from ethyl acetate gave the dihydrochloride salt of the product (1.60 g, 31%) m.p. 171°–175° C. as lilac crystals (Found: C, 58.2; H, 7.3; N, 8.2. $C_{25}H_{35}N_3O_2S. 2HCl$ requires C, 58.4; H, 7.25; N, 8.2.

EXAMPLE 3

4,5,6,7-Hexahydro-1-[2-[1-(1H-imidazolyl)]-[4-[1[4-(2-methoxyphenyl)piperazinyl]]]butyryl-1H-azepine (1) A solution of imidazole (1.36 g, 10 mmol) in dry N, N-dimethylformamide (10 ml) was added to a stirred suspension of sodium hydride (60% dispersion; 0.80 g, ca. 20 mmol) in dry N, N-dimethylformamide (20 ml).

The solution was stirred under argon at room temperature for 30 min, and a solution of 1-chloroacetyl-2,3,4,5,6,7-hexahydro-1H-azepine (3.53 g, 20 mmol) in dry N,N-dimethylformamide (10 ml) was added. The mixture was stirred under argon at room temperature for 2 h and water (4 ml) was added. The mixture was concentrated in vacuo, and the residue was triturated with acetonitrile (75 ml). The mixture was filtered, the filtrate concentrated in vacuo, and triturated with toluene to give 2,3,4,5,6,7-hexahydro-1-[1-(1H-imidazolyl)-]acetyl-1H-azepine (3.07 g) as the free base, m.p. 102°-105° C. A solution of the product in methanol was acidified with ethereal hydrogen chloride. The solution was concentrated in vacuo and the residue was dissolved in hot acetonitrile and filtered. The filtrate was concentrated in vacuo and the crystalline product collected to give 2,3,4,5,6,7-hexahydro-1-[1-(1H-imidazolyl)]acetyl1H-azepine as the hydrochloride quarter hydrate, m.p. 174°-177° C.

(Found: C, 53.2; H, 7.6; N, 17.0. $C_{11}H_{17}N_3O \cdot HCl$ $0.25H_2O$ requires C, 53.2; H, 7.5; N, 16.9%). The hydrochloride salt was reconverted to the free base.

(2) 2,3,4,5,6,7-hexahydro-1-[1-(1Himidazolyl)]acetyl-1H-azepine (2.07 g, 10 mmol) was added to a stirred suspension of potassium hydride (35% dispersion; 2.29 g, ca. 20 mmol) in dry toluene (20 ml) under argon. The suspension was stirred at room temperature for 1 h, and a solution of 1-(2-chloroethyl)-4-(2-methoxyphenyl)piperazine (2.29 g, 9 mmol) in dry toluene (10 ml) was added dropwise. The mixture was stirred under argon at room temperature for 17 h, and was heated at 90° C. for 24 h. Water (20 ml) was added, the layers were separated, and the aqueous phase was extracted with ethyl acetate (2×50 ml). The combined organic phases were washed with water (50 ml) and concentrated in vacuo to give an orange oil (3.37 g). The product was chromatographed on basic $Al_2O_3$ with eluant ethyl acetate:hexane, 2:3 → 1:0 to give 2,3,4,5,6,7-hexahydro-1-[2-[1-(1H-imidazolyl)]-4-[1-[4-(2-methoxyphenyl)-piperazinyl]]]butyryl-1H-azepine as the free base (1.58 g). A solution of the product in methanol was acidified with ethereal hydrogen chloride. The solution was concentrated in vacuo, and the residue was triturated with acetonitrile to give the product as its trihydrochloride salt (1.35 g).

EXAMPLE 4

N-Methyl-3-(4-phenylpiperazin-1-yl)-2-(4-pyridyl)-propanamide

This compound is prepared following the procedure of Example 1 using 1-phenyl-4pyridyl)ethyl]piperazine in place of 1-(2-methoxyphenyl)-4-[1-(2-pyridyl)ethyl]-piperazine and methylisocyanate in place of tert-butylisocyanate.

EXAMPLE 5

N-tert-Butyl-3-[4-(3-chlorophenyl)piperazin-1-yl]-2-(2-quinolinyl)propanamide

This compound is prepared following the procedure of Example 1 using 1-(3-chlorophenyl)-4-[1-(2-quinolinyl)ethyl]piperazine in place of 1-(2-methoxyphenyl)-4-[1-(2-pyridyl)ethyl]piperazine.

EXAMPLE 6

N,N-Dimethyl-4-[(3-trifluorophenyl)piperazin-1-yl]-2-(2-furanyl)butanamide

This compound is prepared following the procedure of Example 2 using N,N-dimethyl-2-(2-furanyl)acetamide in place of 2,3,4,5,6,7-hexahydro-1-[2-(2thiophenyl)acetyl]-1H-azepine and 1-(2-chloroethyl)-4-(3-trifluorophenyl)piperazine in place of 1-(2- chloroethyl)-4-(2-methoxyphenyl)piperazine.

We claim:

1. A compound of the formula $$\underset{R^1-N}{\overset{R}{\diagup\diagdown}}\underset{\diagdown\diagup}{\overset{R^3}{\underset{|}{N-A-CR^2-CONR^4R^5}}} \quad (I)$$

wherein

A is an alkylene chain of 1 or 2 carbon atoms optionally substituted by one or more lower alkyl groups, m is 0, 1 or 2, R is hydrogen or lower alkyl, $R^1$ is aryl or a mono- or bicyclic heteroaryl radical of from 1 to 11 ring atoms having one or two hetero atoms selected from N, O or S which may be optionally substituted as for aryl, $R^2$ is hydrogen or lower alkyl, $R^3$ is a mono- or bicyclic heteroaryl radical of from 5 to 11 ring atoms having one or two hetero atoms independently selected from N O or S, or having three or four N atoms, which may be optionally substituted as for aryl, $R^4$ is hydrogen, lower alkyl or aryl, and $R^5$ is hydrogen, lower alkyl, cycloalkyl, cycloalkyl(-lower)alkyl, aryl, or aryl(lower)alkyl or $R^4$ and $R^5$ together with the nitrogen atom to which they are both attached represent a saturated heterocyclic ring which may contain one further N, O or S hetero atom, wherein aryl refers to an aromatic radical having 6 to 12 carbon atoms which may be optionally substituted by one to three substituents selected from lower alkyl, lower alkoxy halogen, halo(lower)akyl, nitro, amino, and mono- or di-(lower)alkylamino.

2. A compound as claimed in claim 1 in which A is —$CH_2$— or —$CH_2CH_2$—.

3. A compound as claimed in claim 1 in which $R^2$ is hydrogen.

4. A compound as claimed in claim 1 in which $R^3$ is 2- or 4-pyridinyl, 1-imidazolyl or 2-thiophenyl.

5. A compound as claimed in claim 1 in which —$NR^4R^5$ is piperidino or hexahydroazepino.

6. A compound as claimed in claim 1 which is N-tert.-butyl-3-[4-(2-methoxyphenyl)piperazin-1-yl]-2-(2-pyridyl)propanamide or a pharmaceutically acceptable acid addition salt thereof.

7. A compound as claimed in claim 1 which is 2,3,4,5,6,7-hexahydro-1-[2-(2-thiophenyl)-4-(2-methoxyphenyl)-piperazinyl))]butyryl-1H-azepine or a pharmaceutically acceptable acid addition salt thereof.

8. A compound as claimed in claim 1 which is 2,3,4,5,6,7-hexahydro-1-[2-[1-(1H-imidazolyl)]-4-[1-[4-(2-methoxyphenyl)-piperazinyl]]]butyryl-1Hazepine or a pharmaceutically acceptable acid addition salt thereof.

9. A method of treating anxiety or depression in a mammal, which comprises administering to said mammal an amount of a compound of claim 1 effective to alleviate anxiety or depression.

* * * * *